United States Patent [19]

Nevins et al.

[11] Patent Number: 5,650,287

[45] Date of Patent: Jul. 22, 1997

[54] METHOD OF ASSAYING FOR THE ONCOGENIC STATE OF CELLS

[76] Inventors: Joseph R. Nevins, 100 York Pl., Chapel Hill, N.C. 27514; Srikumar C. Chellappan, 311 S. LaSalle St., #23E, Durham, N.C. 27705

[21] Appl. No.: 196,907

[22] Filed: Feb. 15, 1994

Related U.S. Application Data

[63] Continuation of Ser. No. 891,654, May 29, 1992, abandoned, which is a continuation-in-part of Ser. No. 827,387, Jan. 29, 1992, abandoned.

[51] Int. Cl.⁶ .................. G01N 33/574; G01N 33/53; G01N 33/48; C12Q 1/68
[52] U.S. Cl. .................. 435/7.23; 435/6; 435/7.1; 436/63; 436/64
[58] Field of Search .................. 435/6, 7.23; 424/64

[56] References Cited

PUBLICATIONS

Bagchi et al (1991) Cell 65: 1063–1072.
Chellappan (1991) Cell 65: 1053–1061.
S. Bagchi et al., Cell 62, 659–669 (1990).
S. Bagchi et al. Cell, 65, 1063–1072 (1991).
S. Chellappan et al., Cell 65, 1053–1061 (1991).
J. Decaprio et al., Cell 58, 1085–1095 (1989).
N. Dyson et al., J. Virol. 64, 1353–1356 (1990).
S. Hiebert et al., Proc. Natl. Acad. Sci. USA 86, 3594–3598 (1989).
J. Horowitz et al., Proc. Natl. Acad. Sci. USA 87, 2775–2779 (1990).
I. Kovesdi et al., Cell 45, 219–228 (1986).
M. Mudryj et al., Cell 65, 1243–1253 (1991).
K. Munger et al., EMBO J. 8, 4099–4105 (1989).
J. Pines and T. Hunter, Cell 58, 833–846 (1989).
M. Scheffner et al., Proc. Natl. Acad. Sci. USA 88, 5523–5527 (1991).
P. Whyte et al., Nature 334, 124–129 (1988).
A. Yee et al., Mol. Cell. Biol. 9, 578–585 (1989).
L. Bandara et al., Nature 351, 494 (1991).

*Primary Examiner*—Lila Feisee
*Assistant Examiner*—Yvonne Eyler

[57] ABSTRACT

The present invention provides methods for detecting the oncogenic state of cells by detecting the complex formation between the E2F transcription factor and the retinoblastoma (Rb) protein. A first embodiment is a diagnostic assay for detecting the state of Rb function of cells by collecting a cell sample and then detecting free E2F in the cell sample, the presence of free E2F indicating the loss of Rb function of the cells. A second embodiment is a bioassay for screening test compounds for the ability to inhibit the oncogenic state of cells. The bioassay comprises contacting a test compound to a cell capable of producing a complex of the Rb protein and the E2F transcription factor, the cell containing a virus expressing a viral oncoprotein capable of disrupting the complex, and then detecting the appearance of the E2F-Rb complex in the cells, the presence of the E2F-Rb complex indicating the oncogenic state of said cells.

23 Claims, 9 Drawing Sheets

E2F is a Cellular Target for RB 1055

FIG. 2B

E2F is a Cellular Target for RB 1055

E2F$_{cyclin}$ →
E2F$_{Rb}$ →
E2F →

METHOD OF ASSAYING FOR THE ONCOGENIC STATE OF CELLS

This invention was made with Government support under grant number GM 26765 from the National Institutes of Health. The government has certain rights to this invention.

This is a continuation of application Ser. No. 07/891,654 filed on 29 May 1992 and now abandoned, which is a continuation in part of Ser. No. 07/827,387, filed 29 Jan. 1992, now abandoned.

FIELD OF THE INVENTION

This invention relates to the use of the E2F transcription factor to detect oncogenic activation events of cells in bioassays and diagnostic assays.

BACKGROUND OF THE INVENTION

The product of the retinoblastoma susceptibility gene (RB1), a 110 kD nuclear protein, has been implicated in the etiology of a variety of human tumors. In addition to rare retinoblastomas, alteration of RB1 function is likely a major contributing factor in the development of cervical carcinomas. In the majority of cervical carcinomas, the inactivation of the function of the Rb protein is a consequence of the ability of a product of the human papillomavirus gene E7 product to form a complex with Rb.

Until now, the normal function of the Rb protein has been unknown. It has been clear that viral oncoproteins such as adenovirus E1A, SV40 T antigen, and human papillomavirus E7 can target the Rb protein, forming a physical complex that has been believed inactive with respect to Rb function. See Dyson et al., *Science* 243, 934–937 (1989); Whyte et al., *Nature* 334, 124–129 (1988); DeCaprio et al., *Cell* 54, 275–283 (1988). It is also believed that this action of E7 is likely an important event in the development of a majority of human cervical carcinomas. Scheffner et al., *Proc. Natl. Acad. Sci. USA* 88, 5523–5527 (1991). Therefore, therapeutic strategies to intervene in this process would be directed at disrupting this interaction, resulting in a release of Rb so as to allow it to return to its normal function. Until now, this normal function has been unknown. The present invention is based upon our ongoing research in this area.

SUMMARY OF THE INVENTION

We have found that a normal cellular target for Rb is the E2F transcription factor. Since the interaction of E2F with the Rb protein can be readily measured, this finding makes possible bioassays to measure the effectiveness of therapeutic strategies directed at preventing the disruption of the Rb-E2F complex. Moreover, given that the interaction of E2F with Rb appears to be an important aspect of Rb function as a tumor suppressor protein, assay for E2F is also useful as a diagnostic method for cancer.

A first aspect of the present invention is a diagnostic assay for detecting the oncogenic state, with respect to the action of the RB protein, in a human or animal cell. The assay comprises, first, collecting a cell sample and then detecting free E2F or the E2F-Rb complex in the cell sample. The presence of free E2F indicates the loss of RB function in the cells (and hence oncogenic activation) and the appearance of E2F-Rb complex indicates a return to normal Rb function.

A second aspect of the present invention is a bioassay for screening test compounds for the ability to reverse or inhibit the oncogenic activation of cells. The assay involves the use of E2F to measure the release of Rb from complexes with viral oncoproteins such as E7. Reagents that may disrupt such a complex can be screened in conjunction with E2F, ultimately measuring the formation of the E2F-Rb complex. The assay is simple, fast and efficient. Moreover, since it reflects the normal function of the Rb protein, this is not only a simple bioassay, but it is also a relevant assay. The assay comprises, first contacting (e.g., by adding) a test compound to an aqueous solution (e.g., a cell extract solution) that contains a complex of the Retinoblastoma (Rb) protein and a viral oncoprotein such as E7, preventing the interaction of Rb with the E2F transcription factor. The release of Rb from the complex with the viral oncoprotein is then scored by the addition of E2F (e.g., partially purified E2F) and assay (i.e., determining) the formation of the E2F-Rb complex. Subsequently, the assay would involve contacting a test compound to an intact cell capable of producing a complex of the Retino-blastoma (Rb) protein and the E2F transcription factor, and wherein the cell contains a virus expressing a viral oncoprotein capable of disrupting the complex, followed by detecting the loss of free E2F in the cell and the appearance of the E2F-Rb complex. The appearance of the E2F-Rb complex indicates the loss of oncogenic activation of the cell by the test compound.

A third aspect of the present invention is a method for detecting, in a human or animal subject, the oncogenic activation of a cell caused by a mutation in the E2F gene sequence. The method comprises, first, collecting a sample cell from the subject, then amplifying the E2F gene sequence in the sample cell, and then detecting the presence or absence of a mutation in the E2F gene sequence which prevents the E2F transcription factor coded for by the amplified gene sequence from binding to the retinoblastoma protein. The presence of such a mutation indicates the oncogenic activation of the sample cell.

A fourth aspect of the present invention is a DNA binding assay for detecting compounds useful for inhibiting cell proliferation. The assay comprises combining a test compound with a solution containing E2F and a DNA sequence which binds E2F, and then detecting whether or not the test compound inhibits the binding of E2F to said DNA sequence. The inhibition of binding indicates that the test compound may be useful for inhibiting cell proliferation. This assay may be carried out in vitro or in vivo.

The foregoing and other objects and aspects of the present invention are explained in detail in the Figures, Detailed Description and Examples set forth below.

DETAILED DESCRIPTION OF THE INVENTION

As noted above, the present invention provides a diagnostic assay for detecting the state of Rb function in cells, as measured by the interaction with the E2F transcription factor. This comprises first, collecting a cell sample and then assaying the state of E2F in the cell sample, the presence of free E2F indicating the loss of Rb function. The cells can be those of any tissue, including (but not limited to) cervical, retina, bone, lung, bladder, prostate, mammary, and white blood cells. Cervical cells are particularly preferred.

The basis for the assay relies on the ability of E2F to interact with the Rb protein, producing a readily detectable DNA binding complex. Therefore, the efficiency of a procedure that attempts to disrupt the interaction of a viral oncoprotein with Rb, releasing Rb, can be assessed by assaying for the formation of the E2F-Rb complex. The step of measuring or detecting free E2F may be carried out by any suitable technique, including (but not limited to) immunoassay (i.e., with an antibody which specifically binds to free E2F), affinity binding assay, (i.e., with a binding partner other than an antibody), and gel retardation assay. Gel retardation may be carried out in accordance with known techniques, see, e.g., A. Yee et al., Mol. Cell. Biol. 9, 578–585 (1989); S. Bagchi et al., supra, but typically involves the steps of incubation of a cell extract with a radioactive DNA fragment that contains the binding sequence of E2F. Non-specific DNA binding is eliminated by the inclusion of an excess of DNA from calf thymus or salmon sperm. The formation of a specific DNA-protein complex is assayed by electrophoresis of the sample in a non-denaturing (native) polyacrylamide gel followed by autoradiography.

The present invention also provides a bioassay for screening test compounds for the ability to inhibit the oncogenic activation of cells, with the assay comprising contacting a test compound (e.g., a protein, peptide, or small organic compound) to a cell extract derived from a cell that contains a virus expressing a viral oncoprotein that complexes with the Rb protein, preventing the interaction of Rb with E2F in the cell. Upon addition of the test compound, the release of Rb from the complex with the viral oncoprotein is measured by the addition of E2F followed by an assay for the formation of the E2F-Rb complex. The formation of the E2F-Rb complex is thus an indication of the release of the functional Rb protein from the previous interaction with the viral oncoprotein. The ability of the test compound to disrupt the Rb-viral oncoprotein interaction, allowing Rb to complex with E2F, can also be measured in an intact cell. Any suitable cells can be employed, with human cells preferred; any suitable virus, such as adenovirus or human papillomavirus, may be employed. The cells should be ones which can be infected with a virus as given above, e.g., human cervical cells infected with the human papillomavirus. The detecting step may be carried out in the same manner as given above.

The diagnostic method set forth above is adapted to detect oncogenic activation caused by a variety of factors, particularly infection with a virus. However, those skilled in the art will appreciate that, if oncogenic activation can be caused by an external factor (i.e., viral infection) which disrupts the E2F-Rb complex, or by mutation of Rb leading to disruption of the E2F-Rb complex, then oncogenic activation can also be caused by a mutation in the E2F gene sequence which disrupts E2F-Rb complex formation. Hence, a diagnostic assay can comprise collecting a sample cell from a human or animal subject, then amplifying the E2F gene sequence in said sample cell by means such as the polymerase chain reaction process, and then detecting the presence or absence of a mutation in the E2F gene sequence which prevents the E2F transcription factor coded for by the gene sequence from binding to the Rb protein. Subjects and cells employed in this method may be the same as given in connection with the diagnostic method described above. The PCR process can be carried out in accordance with known techniques. See, e.g., K. Mullis, U.S. Pat. Nos. 4,683,195 and 4,683,202 (the disclosures of which are incorporated herein by reference). Purified E2F transcription factor is known. See A. Yee et al., Mol. Cell Biol. 9, 578–585 (1989). The E2F gene sequence is identified and isolated in accordance with known techniques, such as by producing sufficient quantities of purified E2F transcription factor to obtain the amino acid sequence of at least a portion thereof and then probing a genomic DNA or cDNA library with a labelled degenerate oligonucleotide probe which codes for the amino acid sequence to obtain the DNA sequence. See, e.g., F.-K. Lin, DNA Sequences Encoding Erythropoietin, U.S. Pat. No. 4,703,008 (the disclosure of which is incorporated herein by reference); see also K. Jacobs et al., Isolation and Characterization of Genomic and cDNA clones of Human Erythropoietin, Nature 313, 806–810. PCR primers for the E2F gene are made from the E2F gene sequence in accordance with known techniques. See, e.g., K. Mullis, supra.

The basic premise of the DNA binding assay noted above is to utilize the E2F transcription factor as an assay system to screen for compounds that may have utility in the inhibition of cell proliferation. Two assays may be employed for the screening of compounds that may inhibit E2F transcriptional function. The first assay involves an in vitro measurement of the functional capacity of the E2F factor. Since E2F is a DNA binding protein, and this activity can be readily measured in a simple in vitro assay, such an assay scores for the capacity of a test compound to inhibit the ability of E2F to form a specific DNA-protein complex. The assay consists of mixing a preparation of purified E2F with a radiolabeled DNA fragment containing the E2F binding sequence, and then scoring for specific binding by a gel retardation assay. Compounds that inhibit the ability of E2F to bind to DNA are then further screened for specificity by assaying against other DNA binding proteins. The purification of E2F is accomplished by an established procedure using extracts of HeLa cells as the source, and the assay of E2F by gel retardation procedures follows established methods. See A yee et al., supra. Moreover, the assay method is not limited to gel retardation methods. Additional assays can involve more simple filter retention or retention on immobilized beads. With these assays, the test compounds are again assayed for their ability to inhibit the binding of E2F to the specific DNA sequence. A control assay would involve the use of a different DNA binding protein.

A second DNA binding assay for E2F activity scores the in vivo function of E2F as a transcriptional activator. A variety of previous experiments have shown that the E2F binding sites can function as essential promoter elements in transfection assays. This assay consists of measuring the activity of a test gene (for instance, the chloramphenical acetyltransferase (CAT) gene) that is under the control of an E2F-dependent promoter. A stable cell line is constructed that contains the assay gene. The assay gene can be any of several that are readily measured and that are sensitive (for instance, the CAT gene or the luciferase gene). Such a cell line is then used to screen compounds that will inhibit the activity of the promoter, thus reflecting inhibition of E2F activity. A control cell line can be constructed that is identical to the test cell but contained a mutation in the E2F sites such that the promoter would not depend on E2F. An additional control cell line can be constructed that contained the identical test gene but under the control of a distinct transcription factor. In this way, specificity for E2F can be easily established. Further, although the use of a stable cell line would be the simplest form of the assay, it is also possible that the level of expression of the test gene would not be sufficiently high to provide appropriate sensitivity. In this case, transient transfection assays could be employed, using the same test genes, to assay for the inhibitory capacity of the compounds. This test is more laborious but does have the potential for automation, thus allowing for efficiency.

The present invention is explained in greater detail in the following non-limiting Examples. In these Examples, "RPMI" means "Roswell Park Memorial Institute", "DMEM" means "Dulbecco's Minimum Essential Medium", "HEPES" means (N-[2-Hydroxyethyl] piperazine-N'-[2-ethane sulfonic acid]), "PMSF" means phenylmethylsulfonyl fluoride, "EGTA" means ethylene glycol-bis (β-amino ethyl ether).N,N,N',N'-tetra acetic acid, "EDTA" means "ethylenediaminetetraacetic acid", "DTT" means dithiothreitol, "BSA" means "bovine serum albumin", "µg" means "micrograms", "mM" means "millimolar", "hr" means "hours", "min" means "minutes", and temperatures are given in degrees Centigrade unless otherwise indicated.

EXAMPLE 1

The E2F Transcription Factor is a Cellular Target for the Rb Protein

EXPERIMENTAL PROCEDURES

Cells. U937 and Jurkat cells were maintained as suspension cultures in RPMI 1640 medium containing 10% fetal calf serum. EJ carcinoma cells and the J82 and MGHU-5 retinoblastoma cell lines were maintained as monolayers in DMEM containing 10% fetal calf serum.

Preparation of Extracts. Whole-cell extracts were prepared in accordance with standard techniques. See, e.g., S. Bagchi et al., Cell 63, 659–669 (1990).

E2F Assays. The assay of E2F-binding activity by gel retardation is carried out in accordance with standard techniques. See, e.g., A. Yee et al., Mol. Cell Biol. 9, 578–585 (1989); S. Bagchi et al., supra. Assays contained 15 µg of whole-cell extract and 0.5 ng of $^{32}$p-labeled DNA probe, which was a EcoRI-HindIII fragment from the ATF(−) adenovirus E2 promoter plasmid (M. Loeken and J. Brady, J. Biol. Chem. 264, 6572–6579 (1989)).

Antibodies. The RB monoclonal antibody Ab1, the RB peptide antiserum Ab2, and the c-fos monoclonal antibody Ab1 were obtained from Oncogene Science. The cyclin A antiserum is a known rabbit antiserum (J. Pines and T. Hunter, Cell 58, 833–846 (1989)), generously provided by J. Pines and T. Hunter. The RB peptide antisera RB138, RB140, and RB147 are known and have been described previously (P. Whyte et al., Nature 334, 124– 129 (1988); R. Bernards et al., Proc. Natl. Acad. Sci. USA 86, 6474–6478 (1989)).

Immunoprecipitations. Whole-cell extracts (100–150 µg) were incubated with the RB-Ab1 monoclonal antibody or one of the peptide antisera for 1 hr at 4° C. in a buffer containing 20 mM HEPES (pH 7.9), 40 mM KCl, 1 mM MgCl$_2$, 0.1 mM EGTA, 0.1 mM EDTA, 0.5 mM DTT, and 3 mg/ml BSA. The mixtures were then further incubated with protein A-Sepharose for 1 hr at 4° C. The beads were centrifuged and washed four times with 800 µl of the same buffer and then treated with 6 µl of the buffer containing 0.8% deoxycholate. The beads were centrifuged, and the supernatant was treated with NP-40 and used for an E2F DNA-binding assay.

DNA Affinity Chromatography. A whole-cell extract was prepared from 3 liters of U937 cells (250 mg of protein) and chromatographed on a heparin-agarose column in accordance with known techniques. See, e.g., A. S. Yee et al., Mol. Cell. Biol. 9, 578–585 (1989). The material eluting at 600 mM KCl was diluted with 4 vol of buffer (20 mM HEPES [pH 7.6], 10% glycerol, 0.1 mM EGTA, 0.1 mM DTT, 0.2 mM PMSF) and incubated with 2 mg of salmon sperm DNA to block nonspecific DNA binding. This preparation was chromatographed on a 1 ml E2F DNA affinity column containing 800 µg of the EcoRI-HindIII fragment from the ATF(−) adenovirus E2 promoter plasmid (Loeken and Brady, supra) or a parallel column containing a polymerized octamer element (ATTTG-CAT) derived as a DdeI-HinfI fragment from the immunoglobulin heavy chain enhancer. The column was washed with the same buffer containing 100 mM KCl and then eluted with buffer containing 600 mM KCl. Fractions of 1 ml were collected.

Western Blot Analysis. Aliquots of whole-cell extract or fractions from the affinity purification were concentrated by TCA precipitation, redissolved in SDS sample buffer, and applied to an 8% SDS-polyacrylamide gel. After electrophoresis, the separated polypeptides were electrophoretically transferred to nitrocellulose. The blot was incubated with an RB peptide antiserum (RB-Ab2; Oncogene Science) (10 µg/ml) followed by incubation with horseradish peroxidase-conjugated protein A (ABC kit; Vector Laboratories).

E1A-Mediated Dissociation of E2F Complexes. The procedures for the synthesis of wild-type 12S E1A protein and the 928 mutant protein in reticulocyte lysates were carried out in accordance with known techniques. See, e.g., S. Bagchi et al., Cell 62, 659–669 (1990).

RESULTS

An E2F-Containing Complex is Recognized by an RB Antibody. The cellular transcription factor E2F, initially identified as a component of the adenovirus E2 promoter transcription complex and a target for transactivation by E1A (I. Kovesdi et al., Cell 45, 219–228 (1986)), is found in all cell types thus far assayed. Although initial experiments utilizing HeLa cell extracts suggested that E2F bound to DNA on its own, recent experiments have shown that E2F is complexed with other cellular factors in most cell types (S. Bagchi et al., supra).

Figure 1:
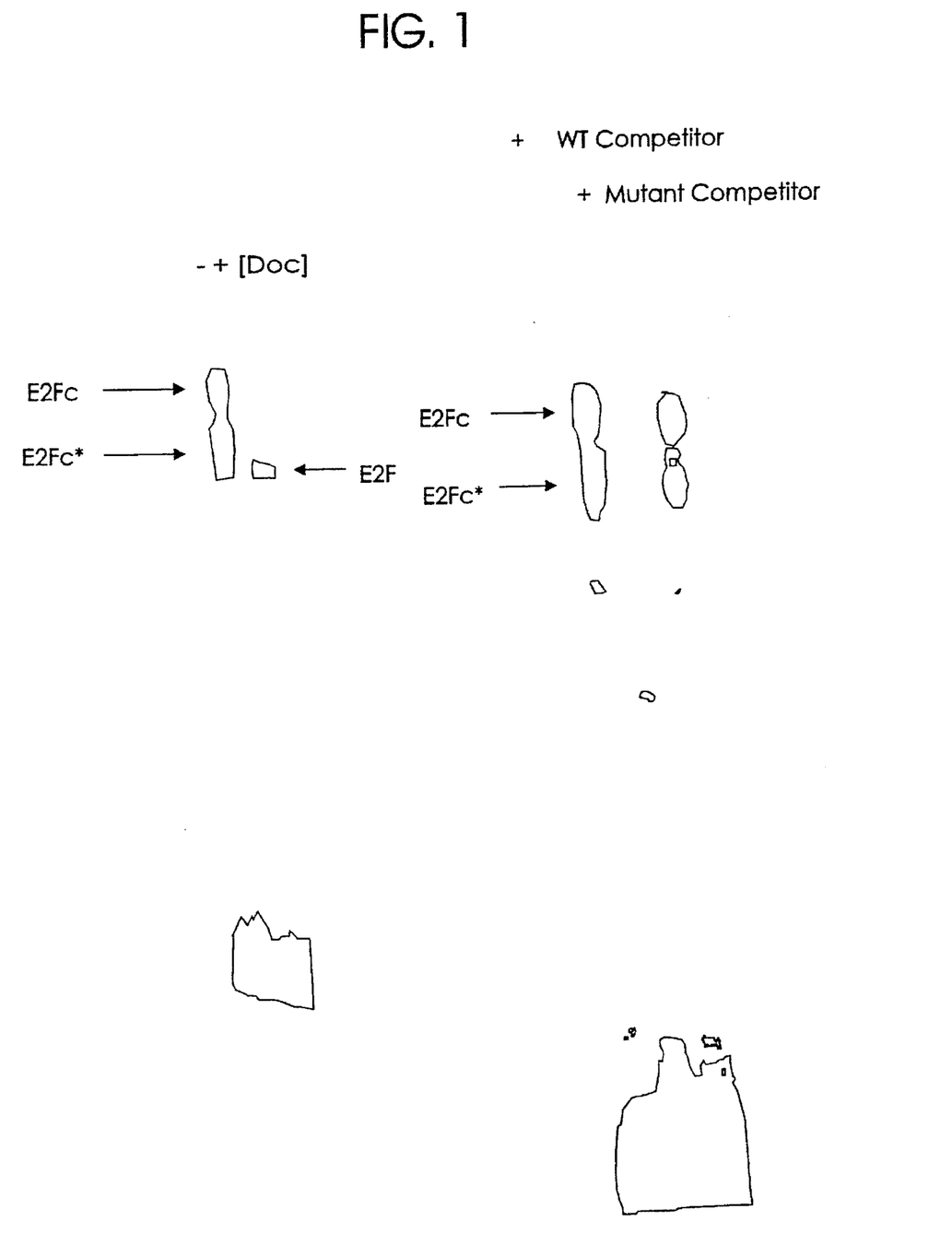
FIG. 1 shows that extracts of U937 cells contain multiple E2F complexes. (Left) Dissociation by deoxycholate. (Right) Sequence specificity of DNA binding.

FIG. 1 shows that extracts of U937 cells contain multiple E2F complexes. FIG. 1 (left) shows dissociation by deoxycholate. E2F-binding assays utilized a whole-cell extract (15 µg) prepared from U937 cells and a DNA probe (0.5 ng) that derives from the adenovirus E2 promoter. One-half of the sample was treated with deoxycholate followed by NP-40 prior to the assay for DNA binding. Two major DNA-protein complexes, labeled $E2F_c$ and $E2F_{c*}$, are detected by this assay. An additional, minor complex that migrates between the two major species is not reproducibly observed. If the extract is first treated with deoxycholate and then assayed for E2F binding, the initial complexes are converted into a single DNA-protein complex that is typical of the interaction of a free E2F factor with the DNA, based on our previous observations (S. Bagchi et al., supra).

FIG. 1 (right) shows the sequence specificity of DNA binding. E2F binding was assayed on the E2 promoter probe in the presence of 200 ng of cold wild-type competitor DNA or 200 ng of a competitor DNA with a mutation in the E2F recognition site that has previously been shown to eliminate E2F binding (Hiebert et al., Proc. Natl. Acad. Sci. USA 86, 3594–3598 (1989)). Competition with a DNA probe containing the wild-type E2F recognition sequence but not a mutant E2F recognition sequence demonstrates the specificity of the interactions.

Previous experiments have shown that the adenovirus E1A protein can dissociate E2F-containing complexes, releasing free E2F (S. Bagchi et al., supra). Although the precise mechanism for this dissociation has not been established, one possibility could involve a direct interaction of E1A with the complex, displacing E2F and leaving E1A associated with the protein originally bound to E2F. There are, of course, a number of candidates for the protein that would be left in a complex with E1A; these are the proteins that are co-immunoprecipitated with E1A in extracts of E1A-expressing cells (S. Yee and P. Branton, Virology 147, 142–153 (1985); E. Harlow et al., Mol. Cell. Biol. 6, 1579–1589 (1986). Indeed, one such protein, cyclin A, is involved in an interaction with E2F that is dissociated by the E1A protein (M. Mudryj et al., Cell (1991). Of course, the product of RB1 is another E1A-associated protein that is a potential candidate for an E2F-binding protein (Whyte et al., supra).

Figure 2A:
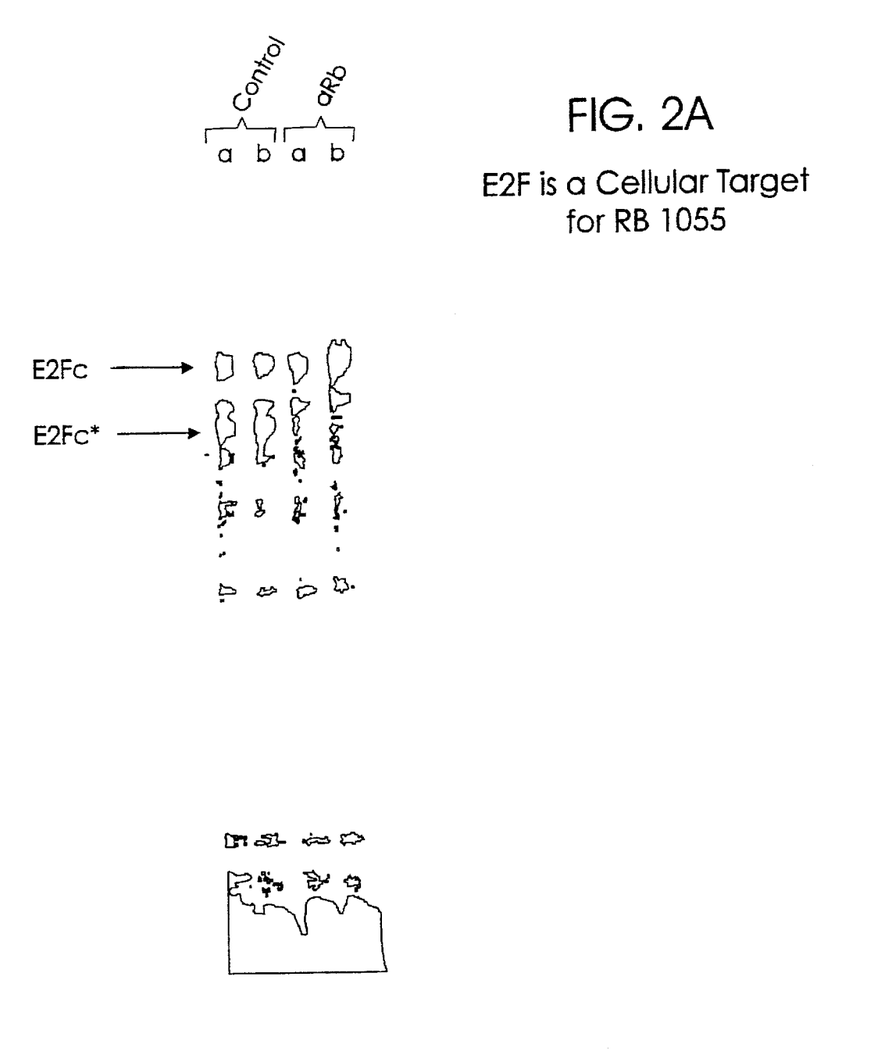
FIG. 2 shows that an E2F complex contains the RB Protein. (A) The U937 extract was assayed for E2F binding as in FIG. 1. (B) Separate E2F complexes contain RB and cyclin A.

Using antibodies that recognize the RB protein, we have tested the U937 extracts for the possible involvement of RB in the formation of the E2F-specific complexes. FIG. 2 shows that an E2F complex contains the RB protein. In FIG. 2(A) the U937 extract was assayed for E2F binding as in FIG. 1. Assays were conducted in the presence of a control monoclonal antibody that was raised against the c-fos protein (c-fos Ab1; Oncogene Science) (Control) and an RB-specific monoclonal antibody (RB-Ab1; Oncogene Science) (αRb). In each case, either a 1:4 (lanes a) or a 1:2 (lanes b) dilution was added. The addition of an RB monoclonal antibody to the extract did not alter the slowly migrating $E2F_c$ complex. In sharp contrast, the faster-migrating $E2F_{c*}$ complex was completely eliminated by the addition of the RB-specific monoclonal antibody, thus indicating that this complex did indeed contain the RB protein. The addition of a control antibody (a monoclonal specific to the c-fos protein) to the U937 extract prior to the DNA-binding assay did not alter the pattern of E2F complexes.

Figure 2B:
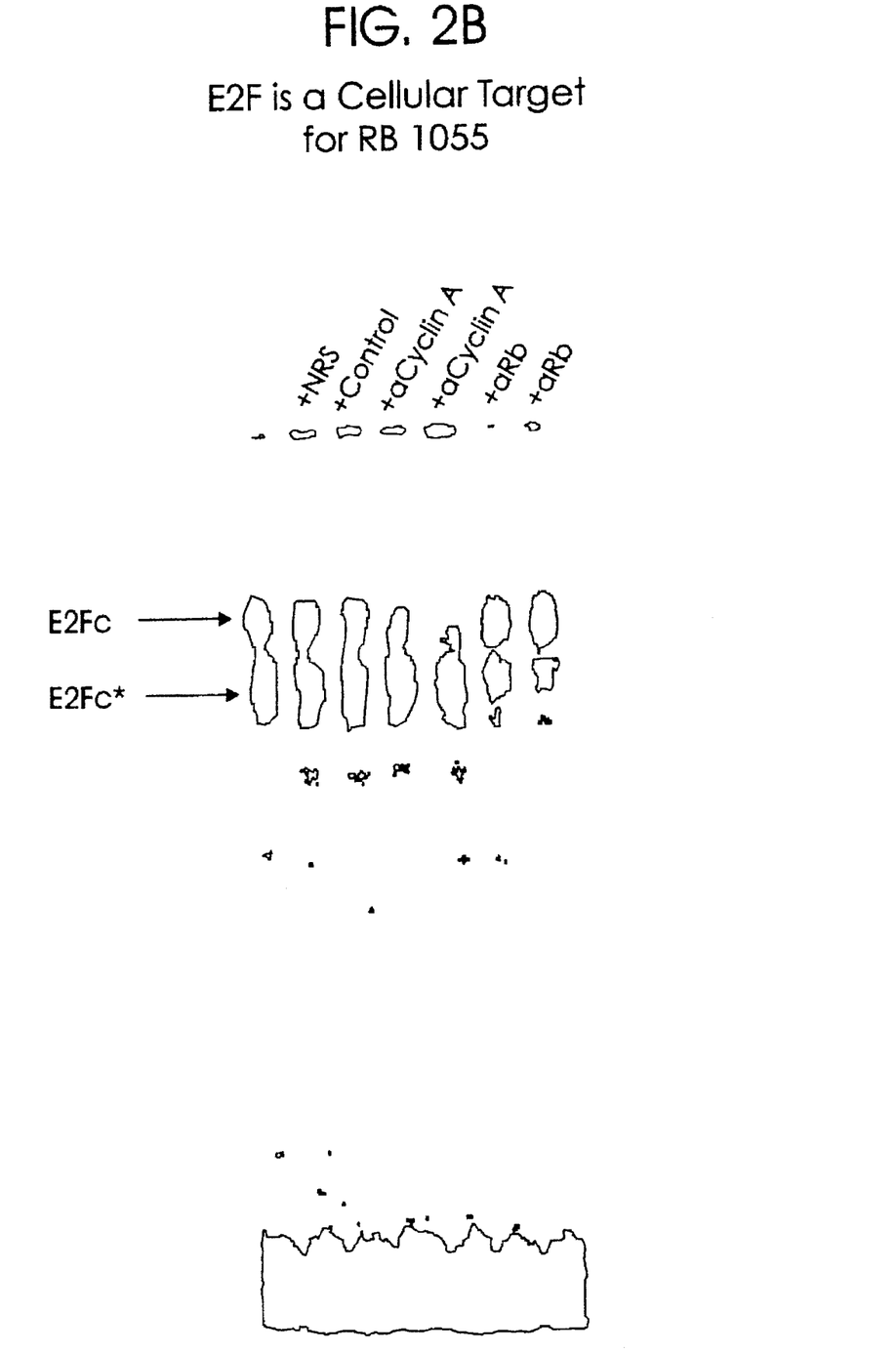

Separate E2F Complexes Contain RB and Cyclin A. Our recent experiments have demonstrated that an S phase-specific E2F-complex in NIH 3T3 cells contains the cyclin A protein (M. Mudryj et al., supra). The mobility of this 3T3 complex is similar to that of the $E2F_c$ complex detected in the U937 extracts. Indeed, as shown in FIG. 2B, the $E2F_c$ complex does involve an interaction with the cyclin A protein. In FIG. 2(b), the U937 extract was again assayed for E2F binding as in FIG. 1. Assays were conducted in the presence of normal rabbit serum (NRS) diluted 1:8, the c-fos control monoclonal antibody (Control) diluted 1:2, a rabbit antiserum specific to the cyclin A protein (αCyclin A) diluted 1:16 (left) or 1:8 (right), and the RB-specific monoclonal antibody (αRb) diluted 1:4 (left) or 1:2 (right). As before, addition of the RB antibody eliminated the faster-migrating $E2F_{c*}$ complex but had no effect on the $E2F_c$ complex. By contrast, addition of the cyclin A antiserum eliminated the $E2F_c$ complex but did not affect the $E2F_{c*}$ complex. It thus appears clear that two distinct E2F complexes can be detected in extracts of growing U937 cells; one involves an interaction with the cyclin A protein and another involves the RB protein. Thus, two of the identified E1A-interacting cellular proteins are found in E2F complexes.

Figure 3A:
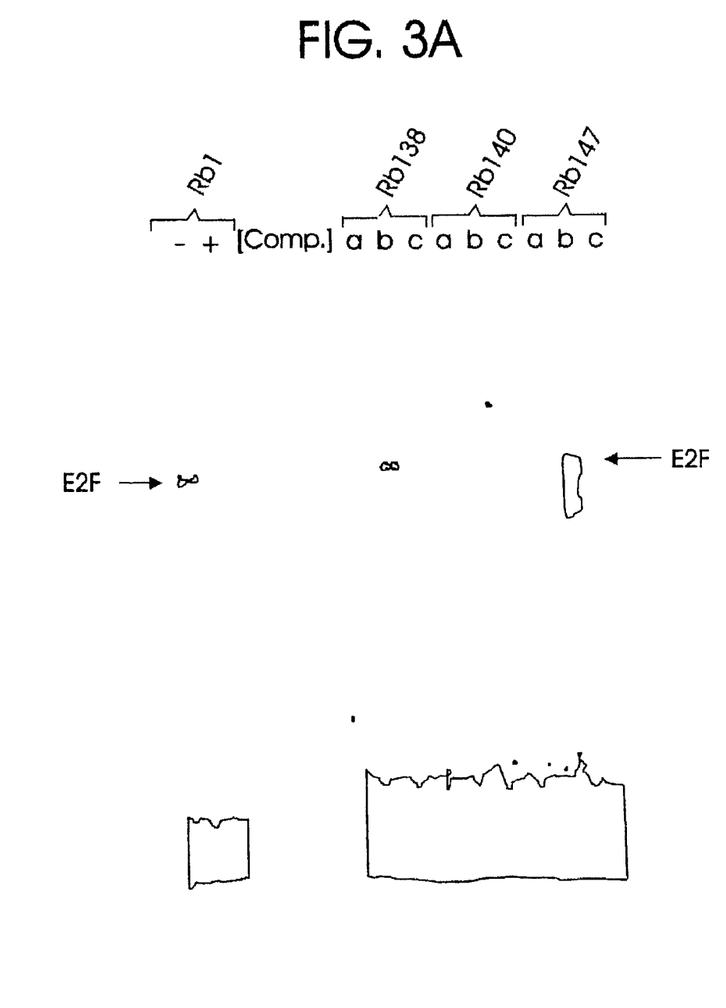
FIG. 3 shows that the E2F-RB complex is not detected in RB negative cells. (A) A U937 whole-cell extract was immunoprecipitated with the RB-Ab1 monoclonal antibody. (B) Immunoprecipitation of extracts of $RB^+$ and $RB^-$ cells.

The E2F-RB Complex is Not Detected in Several RB-Negative Cell Lines. Further evidence that the $E2F_{c*}$ complex was recognized by the RB antibody was provided by an immunoprecipitation analysis. The U937 extract was incubated with an RB monoclonal antibody (RB1), and the immunoprecipitated material was washed and then eluted by the addition of deoxycholate. The released material was then assayed for E2F-binding activity in the presence or absence of an E2F competitor DNA. As seen in FIG. 3A, specific E2F-binding activity was clearly detected in the material immunoprecipitated with RB1. We have also utilized several RB-specific antisera that were raised against synthetic peptides derived from the RB protein sequence. In FIG. 3A, a U937 whole-cell extract was immunoprecipitated with the RB-Ab1 monoclonal antibody. The supernatant after DOC release was treated with NP-40 and assayed for E2F DNA-binding activity. The specificity of the E2F binding assay was demonstrated by performing the assay in the presence or absence of 200 ng of cold probe DNA. (Right) A U937 whole-cell extract was incubated with 10 μl of preimmune serum (lanes a) or the corresponding antiserum raised against an RB peptide (lanes b). To demonstrate the specificity of the coprecipitation, the RB antisera were preincubated with 10 μg of the corresponding peptide prior to the immunoprecipitation (lanes c). Conditions for the immunoprecipitation were the same as used for the monoclonal antibody.

As shown in FIG. 3A, two of the three peptide sera did precipitate E2F activity (lanes b). Moreover, in each case, preimmune antiserum did not coprecipitate E2F (lanes a), and most importantly, the peptide to which the antiserum was raised was able to block the immunoprecipitation (lanes c). That one of the peptide antibodies (RB140) did not immunoprecipitate the complex suggests that this epitope is either hidden in the complex or has an altered conformation when RB is complexed with E2F.

Figure 3B:
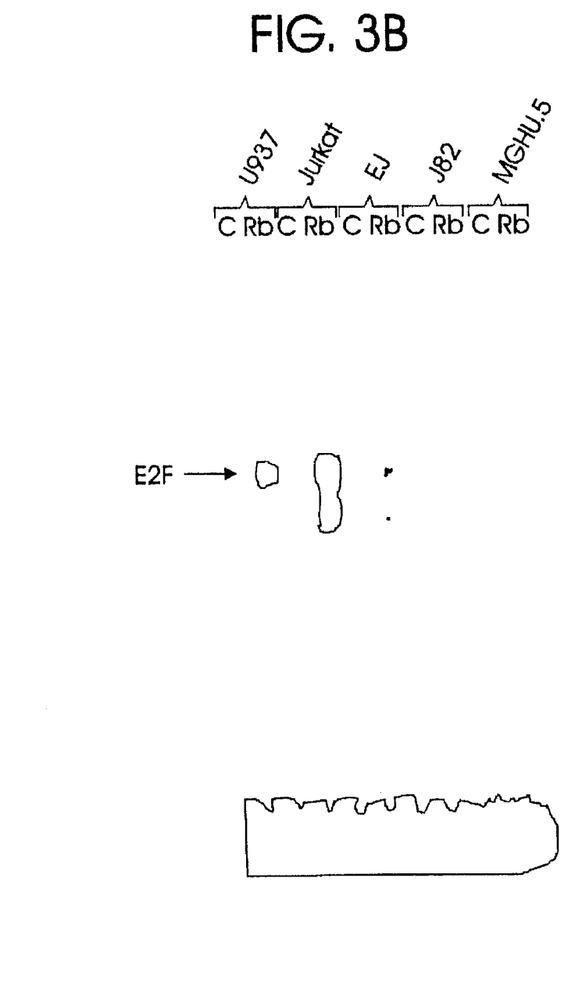

Finally, we have assayed for the E2F-RB interaction in other cell extracts, including two cell lines deficient in functional RB activity. FIG. 3B shows immunoprecipitation of extracts of RB$^+$ and RB$^-$ cells. Immunoprecipitations were carried out as described in (A) using the c-fos monoclonal antibody as a control (lanes C) or the RB-Ab1 monoclonal antibody (Lanes Rb). Whole-cell extracts were prepared from the indicated cell lines, and 100 μg of each was employed for the assay. As shown in FIG. 3B, E2F was coprecipitated with the RB monoclonal antibody from extracts of EJ cells and Jurkat cells as well as the U937 cells. However, we could detect no evidence of E2F coprecipitation from extracts of either J82 cells or MGHU-5 cells, both of which lack functional RB protein (see, e.g., J. Horowitz et al., Proc. Natl. Acad. Sci. USA 87, 2775–2779 (1990). Interestingly, the RB1 gene is expressed in J82 cells but it encodes a mutant form of the RB protein that also fails to interact with E1A (J. Horowitz et al., Science 243, 937–940 (1989)).

The RB protein copurifies with E2F. The experiments presented in FIGS. 2 and 3 strongly suggest that the RB protein is a component of the E2F$_{c+}$ complex. As an additional proof of this interaction, we have reversed the procedure; that is, we have isolated the E2F factor and assayed for the presence of the RB protein. Although an E2F-specific antiserum is not available, it is possible to isolate E2F by DNA affinity chromatography and then assay for the presence of a 110 kd polypeptide that is immunoreactive with the RB monoclonal antibody. A whole-cell extract of U937 cells was fractionated through a heparin-agarose column followed by an E2F-specific DNA affinity column. Fractions from the affinity column eluate were assayed for E2F-binding activity and then fractionated on an SDS-polyacrylamide gel for Western blot analysis with the RB antibody.

Figure 4A:
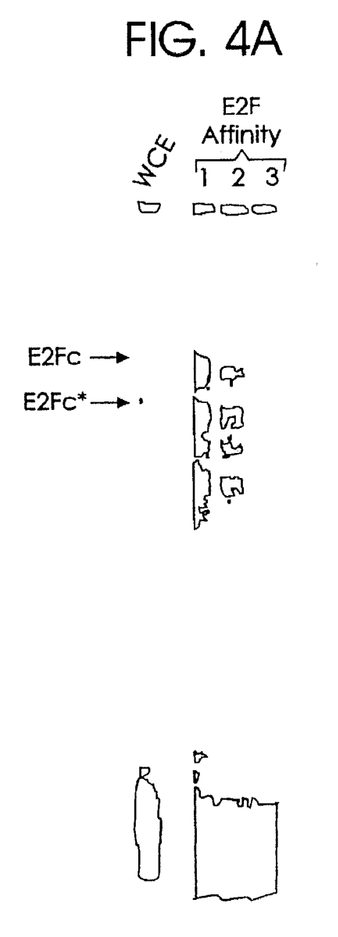
FIG. 4 shows that the RB protein copurifies with E2F. (A) A U937 whole-cell extract was chromatographed on a heparin-agarose column. (B) Western blot assay of samples from affinity purification. (C) RB is specifically retained on the E2F column.
Figure 4B:
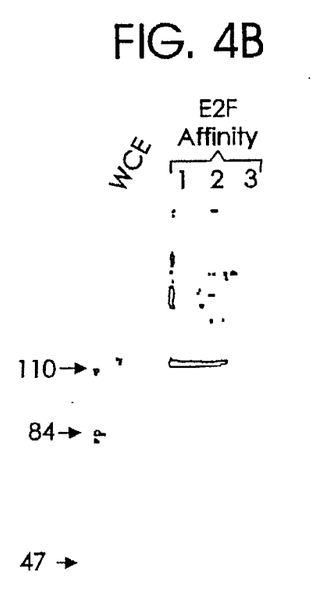
Figure 4C:
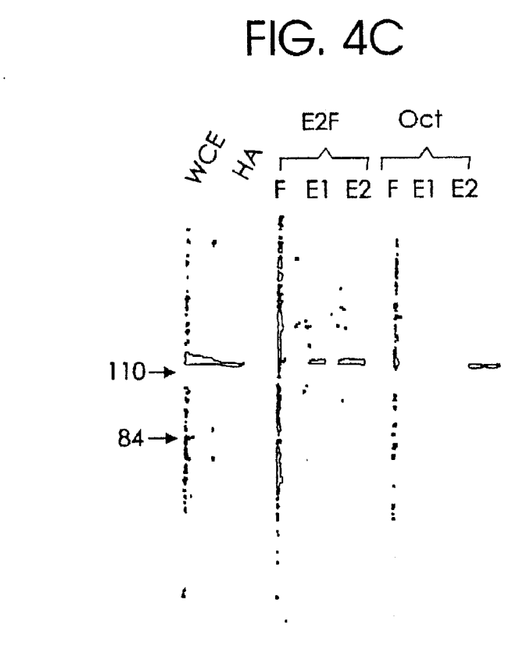

FIG. 4 shows that the RB protein copurifies with E2F. FIG. 4(A) shows a U937 whole-cell extract was chromatographed on a heparin-agarose column. The heparin-agarose eluate was incubated with 2 mg of salmon sperm DNA to block nonspecific DNA binding. This preparation was chromatographed on an E2F DNA affinity column. The column was eluted with buffer containing 600 mM KCl, and 1 ml fractions were collected. E2F-binding activity was assayed (as in FIG. 1) in 1 µl of the whole-cell extract and 3 µl of the affinity eluate fractions. FIG. 4(B) shows a Western blot assay of samples from affinity purification. The affinity column eluate fractions were concentrated by TCA precipitation, redissolved in SDS sample buffer, and applied to an 8% SDS-polyacrylamide gel. In addition, a 30 µl aliquot of the whole-cell extract was also applied to the gel. After electrophoresis, the separated polypeptides were electrophoretically transferred to nitrocellulose. The blot was incubated with an RB peptide antiserum (RB-Ab2; Oncogene Science) at 10 µg/ml followed by incubation with horseradish peroxidase-conjugated protein A (ABC kit; Vector Laboratories). Stained marker proteins are in the left lane. FIG. 4(C) shows that RB is specifically retained on the E2F column. A U937 whole-cell extract was processed as described in (B) and applied in parallel to an E2F affinity column and an octamer-specific affinity column. The two columns were eluted with 600 mM KCl, and 1 ml fractions were collected. The eluate fractions were TCA precipitated and dissolved in SDS sample buffer, and the entire samples were analyzed. Due to high concentration of protein in the affinity column loading material (HA) as well as the affinity flow through fractions (F), only 10% of the volume of these fractions was applied to the gel. Finally, a 30 µl aliquot of the whole-cell extract (WCE) was also analyzed.

As can be seen in FIG. 4B, the 110 kd RB polypeptide, as detected by the RB1 antibody, is indeed detected in the affinity column eluate, coinciding with the presence of the E2F$_{c*}$ complex (FIG. 4A). It should also be noted that the recovery of the RB polypeptide in the E2F affinity column eluate is not likely the result of simple nonspecific DNA binding since the sample is loaded in the presence of a large amount of salmon sperm DNA. This was in fact confirmed by fractionating a U937 extract on two parallel DNA affinity columns, one containing the E2F-binding site and the other containing the octamer element-binding site. As shown in FIG. 4C, the RB protein is again recovered in the E2F affinity eluate but is not recovered in the eluate of the octamer column.

Figure 5:
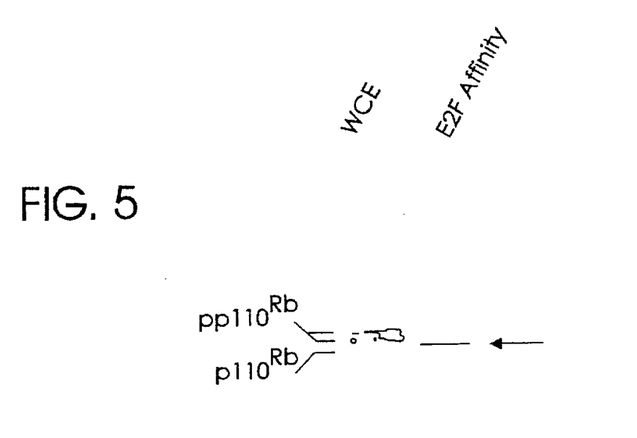
FIG. 5 shows that the underphosphorylated form of RB is in the E2F complex.

A variety of previous experiments have shown that in extracts of asynchronously growing cells there is a mixture of phosphorylated and unphosphorylated forms of the RB protein that can be resolved by SDS-PAGE since the phosphorylated forms of the protein migrate more slowly than the unphosphorylated protein. See, e.g., J. DeCaprio et al., Cell 58, 1085–1095 (1989). It is apparent from the analysis of FIG. 4B that the crude extract (WCE) contains several species that react with the RB antibody, whereas the affinity column eluate appears to contain a single polypeptide. This is more clearly shown in an independent analysis, with improved gel resolution, in which it is evident that the polypeptide in the E2F affinity eluate corresponds to the fastest-migrating species of RB in the whole-cell extract. FIG. 5 shows that the underphosphorylated form of RB is in the E2F complex. Samples of the U937 whole-cell extract and the E2F DNA affinity column eluate of this extract were assayed as in FIG. 4B. Thus, E2F does not appear to interact randomly with the population of RB proteins within the cell, but rather, only the un- or underphosphorylated form of RB is in a complex with E2F. Since the RB protein becomes phosphorylated as the cell leaves G1 (see, e.g., DeCaprio et al., supra), we conclude that the E2F-RB complex must be most prevalent in G1.

E1A Dissociates the E2F-RB Complex. Previous experiments have shown that the adenovirus E1A protein can dissociate E2F-containing complexes, releasing free E2F, and that this activity correlates with the ability of the 12S E1A product to transactivate transcription (Bagchi et al., supra). Moreover, the E1A sequences required for this activity correlate with those required for interaction with the RB protein (Bagchi et al., supra.

Figure 6A:
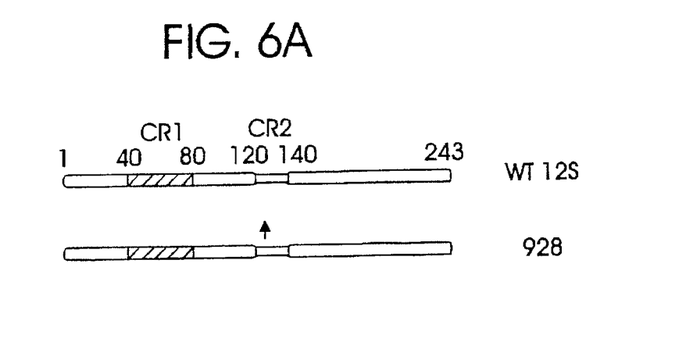
FIG. 6 shows that the Adenovirus E1A protein can dissociate the E2F-RB complex. (A) Schematic depiction of the structure of the wild-type E1A 12S cDNA and the 928 mutant cDNA. (B) Assays for E1A dissociation of the E2F-RB complex. (C) Immunoprecipitation assays.
Figure 6B:
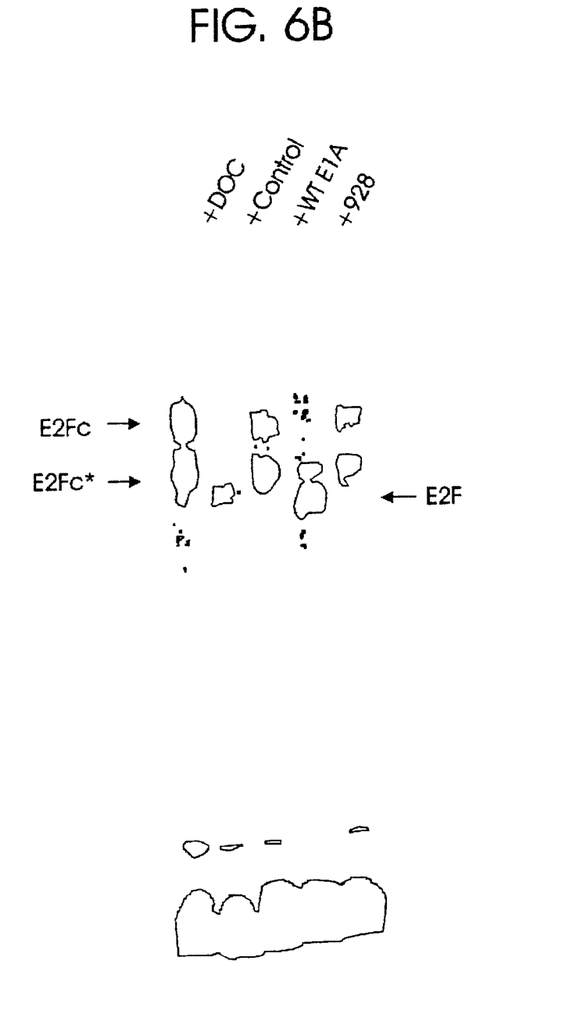
Figure 6C:
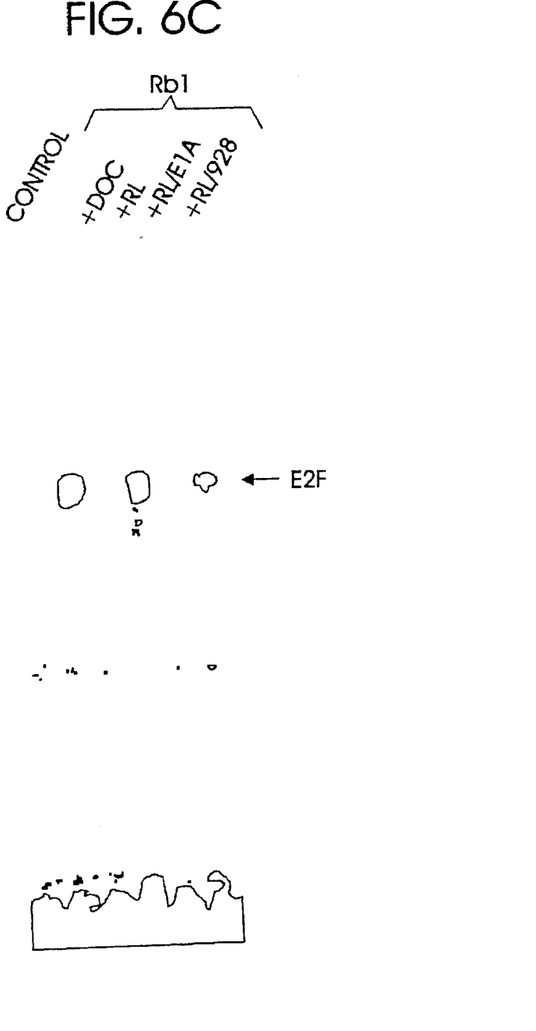

FIG. 6 shows that the Adenovirus E1A protein can dissociate the E2F-RB complex. FIG. 6(A) gives a schematic depiction of the structure of the wild-type E1A 12S cDNA and the 928 mutant cDNA. FIG. 6(B) shows assays for E1A dissociation of the E2F-RB complex. The U937 whole-cell extract (15 µg) was incubated with equal amounts (1 µl) of a reticulocyte lysate programmed with transcripts of the wild-type E1A 12S cDNA or the 928 mutant. After incubation for 15 min, the extract was assayed for E2F DNA-binding activity by gel retardation. A parallel sample of U937 extract was treated with deoxycholate and assayed for E2F. FIG. 6(C) shows immunoprecipitation assays. A U937 whole-cell extract was immunoprecipitated with a control monoclonal or the RB monoclonal antibody as described in the Experimental Procedures given above. Prior to immunoprecipitation with the RB antibody, the extract was incubated for 30 min with 0.8% DOC, or 12 µl of control reticulocyte lysate, reticulocyte lysate programmed with the 12S E1A RNA, or reticulocyte lysate programmed with the 928 mutant RNA.

As shown in FIG. 6, the 12S E1A product can dissociate the majority of the two major E2F complexes found in the U937 cell extract, including the E2F complex that contains the RB protein (E2F$_{c*}$). Moreover, the dissociation of the RB-containing E2F complex is dependent on the CR2 sequence of the E1A protein, as indicated by the failure of the 928 point mutant to dissociate the complex. This conclusion is further supported by immunoprecipitation assays in which the ability of E2F to coimmunoprecipitate with RB was abolished by incubation of the U937 extract with wild-type E1A protein but not the 928 mutant (FIG. 6C). Since this CR2 sequence is also required for E1A to form a stable complex with the RB protein (see, e.g., Whyte et al., supra), we suggest that at least a part of the proposed inactivation of RB function by E1A is a consequence of the ability of E1A to alter the E2F-RB interaction.

EXAMPLE 2

Inactivation of Rb Function in Cervical Carcinoma Cells Coincides With Loss of the E2F-Rb Complex This experiment explores the role of HPV E7 in targeting the E2F-Rb interaction.

Extracts of the human monocytic cell line U937, as well as several other human cell lines, contain an E2F-Rb complex that can be dissociated by the adenovirus E1A protein, dependent on E1A sequence that is involved in binding to the Rb protein. Using these U937 extracts, the HPV 16 E7 protein was tested for its ability to also dissociate the E2F-Rb complex. The U937 extract contains two specific E2F complexes (not shown). The slow-migrating complex contains the cyclin A protein in association with E2F whereas the fast-migrating complex contains the Rb protein in association with E2F.

Figure 7:
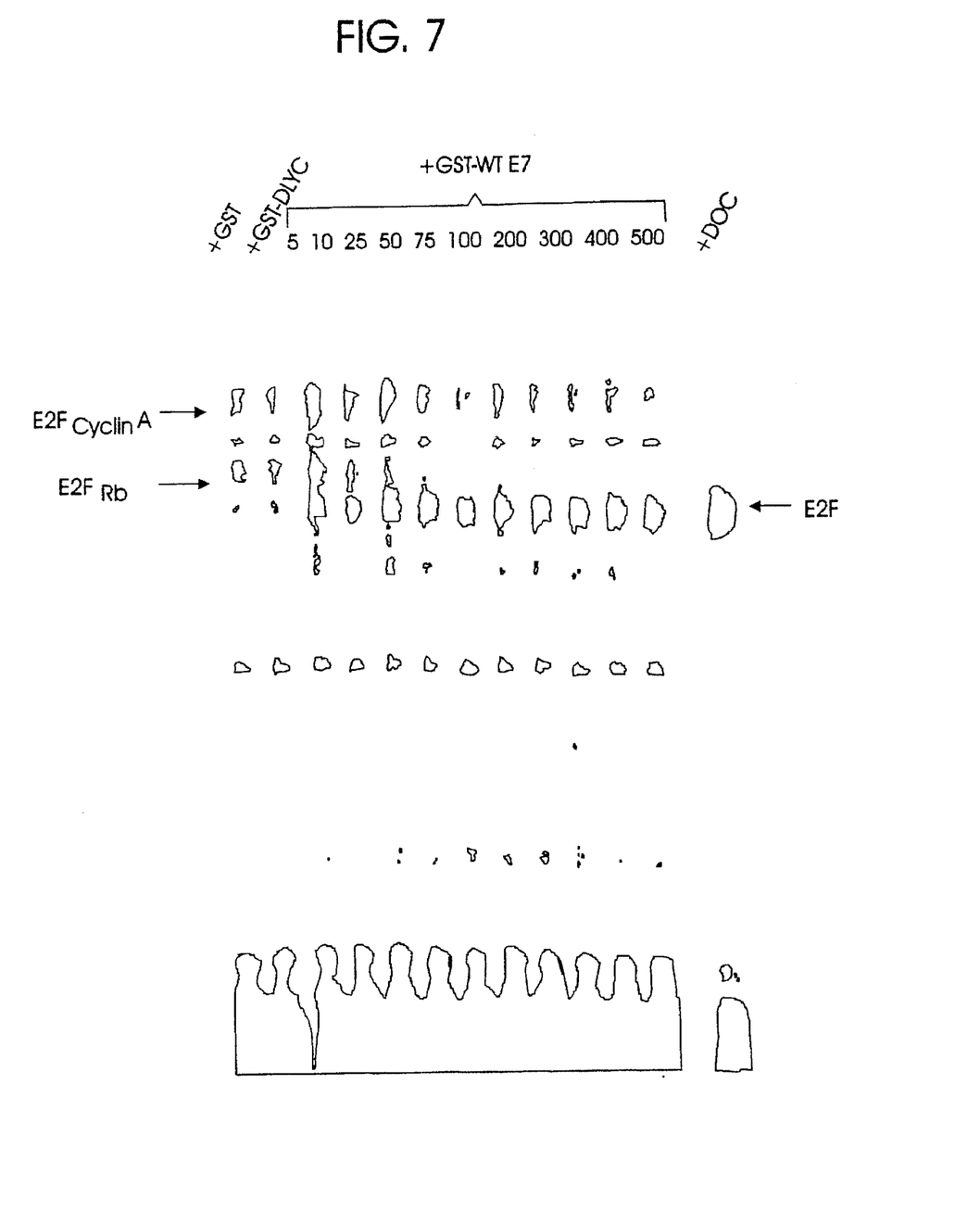
FIG. 7 shows that the HPV E7 protein can dissociate the E2F-Rb Complex.

FIG. 7 shows that the HPV E7 protein can dissociate the E2F-Rb Complex. Extracts of U937 cells were assayed for E2F binding activity in accordance with known techniques. See S. Chellappan et al., Cell 65, 1–9 (1991). The binding assays included a control glutathione-S-transferase (GST) protein (500 ng), the $\triangle$DLYC deletion mutant (GST-DLYC) (500 ng), or increasing amounts (in ng) of the wild type E7 protein (GST-WT E7). In addition, a sample was also incubated with deoxycholate (DOC) prior to the assay. The positions of the E2F-Cyclin A complex and the E2F-Rb complex, as well as the position of free E2F, are indicated.

Addition of the control glutathione-S-transferase (GST) protein to the extract did not alter either of the E2F complexes. In contrast, addition of the WT E7-GST fusion protein eliminated the E2F-Rb complex. Addition of the $\triangle$DLYC mutant of E7, which deletes critical amino acid sequence involved in Rb binding (not shown), did not dissociate the E2F-Rb complex. These data therefore demonstrate that the E7 protein can dissociate the E2F-Rb complex, dependent on the E7 domain known to be involved in Rb binding (K. Munger et al., EMBO J. 8, 4099–4105 (1989)). It is also evident from the assay in FIG. 7 that the E7 protein had only a modest effect on the E2F-Cyclin A complex, in contrast to the efficient dissociation of the E2F complex containing the Rb protein. Whether this is an intrinsic property of the E7 protein or reflects the in vitro assay is not clear at this time.

A recent study has analyzed a series of HPV-positive and HPV-negative human cervical carcinoma cell lines for the state of the RB1 gene. See M. Scheffner et al., Proc. Natl. Acad. Sci. USA 88, 5523–5527 (1991). These studies demonstrated that the HPV-positive cervical cancer cells expressing E7 possessed a normal, wild type Rb protein. In contrast, the HPV-negative cell lines that did not express E7, contained mutant pRb, thus providing strong evidence for the role of Rb inactivation, either by mutation or through its association with E7, in the genesis of these tumors. If regulation of the E2F transcription factor by complex formation is a normal function of RB1 then one might expect to find disruptions of E2F-Rb complexes in these carcinoma cell lines. An analysis of E2F in these cell extracts by direct gel retardation was therefore carried out.

FIG. 8 shows that the E2F-Rb complex is reduced or absent from a variety of human cervical carcinoma cell lines. FIG. 8(A) gives gel retardation assays. Whole cell extracts were prepared from each of the indicated cell lines by known procedures. See S. Chellappan et al., supra. The various cell lines are known. See, e.g., M. Scheffner et al., Proc. Natl. Acad. Sci. USA 88, 5523–5527 (1991). Extracts were prepared from growing cultures. Cell extracts were assayed for E2F binding activity as described in S. Chellappan et al., supra. The three panels represent three different assays and in each case, the U937 sample was used as the basis for comparison. FIG. 8(B) gives co-immunoprecipitation assays. Cell extracts were incubated with either the cyclin A antiserum or the Rb monoclonal antibody as described in S. Chellappan et al., supra, see also M. Mudryj et al., Cell 65, 1243–1253 (1991). Immunoprecipitates were washed, incubated with DOC to release E2F, and then E2F binding activity was measured in the supernatant.

Figure 8A:
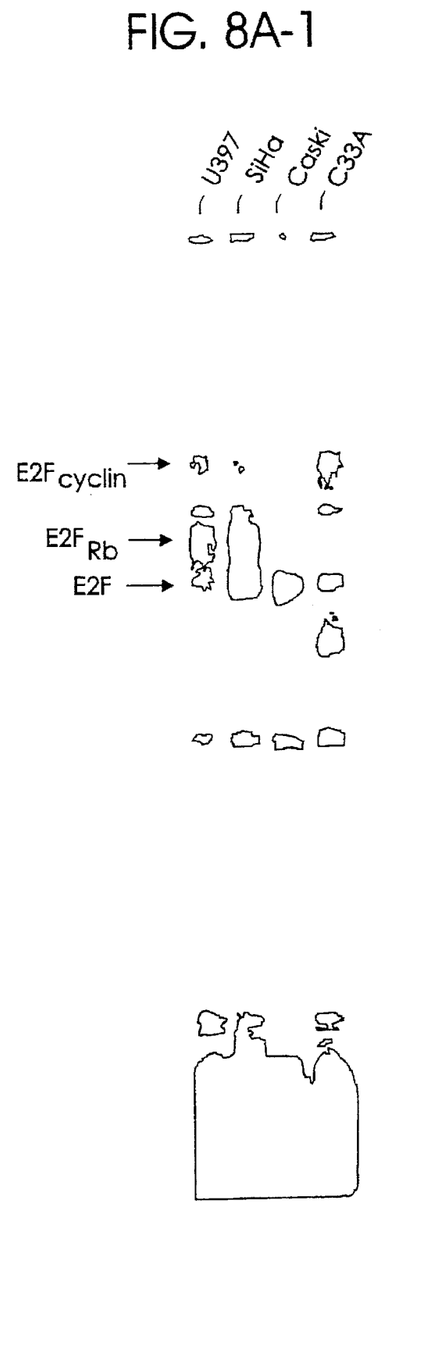
FIG. 8 shows that the E2F-Rb complex is reduced or absent from a variety of human cervical carcinoma cell lines. (A) Gel retardation assays. (B) Co-immunoprecipitation assays.
Figure 8A:
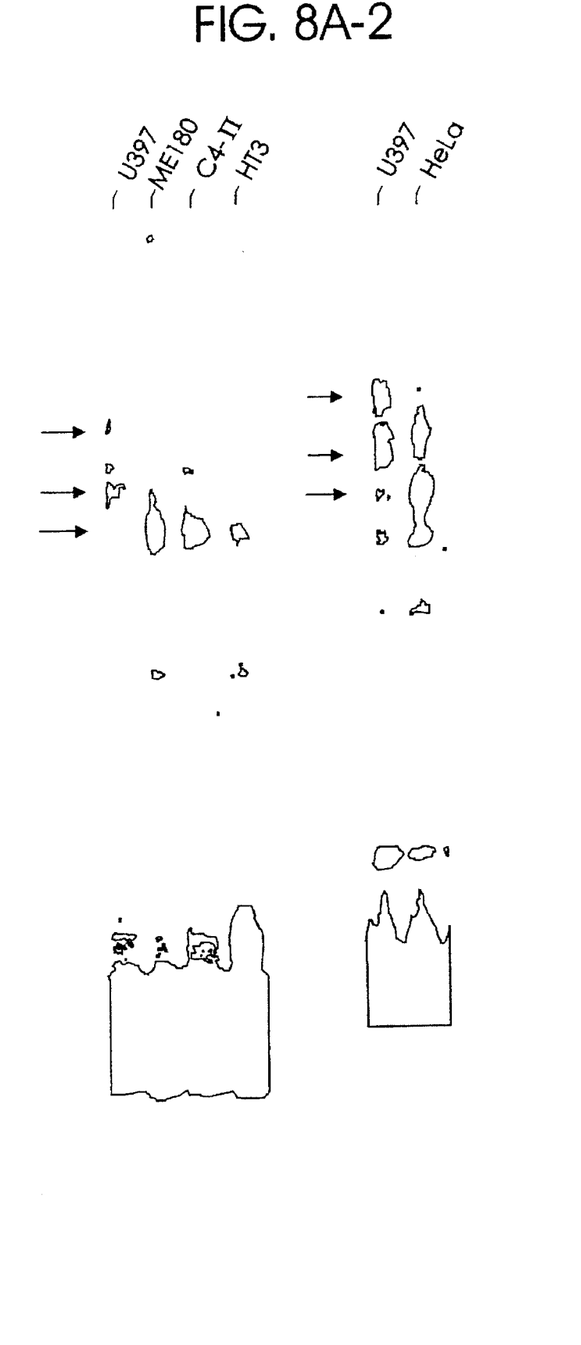
Figure 8B:
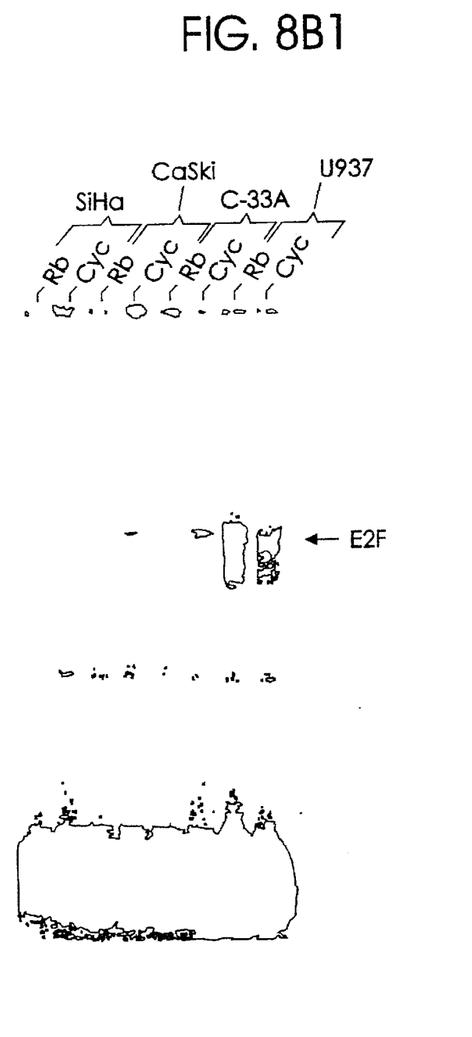
Figure 8B:
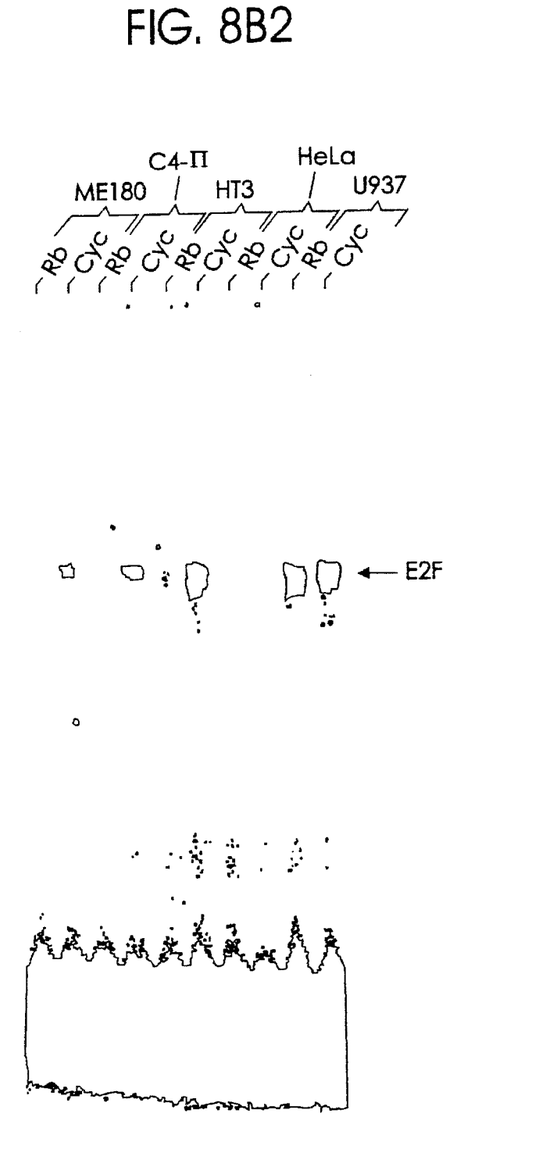

As shown in FIG. 8A, the E2F-cyclin A complex was detectable in each extract with the exception of HeLa cells in which it was greatly reduced. The E2F-Rb complex was absent from each of the samples with the exception of the SiHa extract where there appeared to be a significant amount of the complex, equal to that found in the U937 extract. Again, this may reflect the low level of E7 expression in SiHa cells. It is also evident from these assays that there are significant amounts of free E2F in each of the cervical carcinoma cell extracts. Indeed, if one compares the amount of free E2F to E2F in a complex, it is clear that in most cases the majority of E2F is uncomplexed. In addition to the ability of E7 to dissociate E2F from the E2F-Rb complex as demonstrated in FIG. 7, this appearance of free E2F may also reflect the ability of E7 to block the action of an inhibitor of E2F DNA binding, which also appears to involve the Rb protein (S. Bagchi et al., Cell 65, 1063–1072 (1991). From these results, we conclude that the E2F-Rb interaction is specifically lost in those cells that express an altered form of the Rb protein or in those cells that express high levels of the HPV E7 protein. Coincident with the loss of the E2F-Rb complex is the increase in levels of free E2F. The fact that E2F-cyclin A complexes were found in many of the E7-expressing cells suggests that the E7 protein may not efficiently disrupt the E2F-cyclin A interaction, a conclusion consistent with the in vitro dissociation assays of FIG. 7.

These results were further verified by E2F co-precipitation experiments using antibodies specific for cyclin A or pRb. Previous experiments have shown that E2F is co-immunoprecipitated with the Rb protein from extracts of cells that express a normal, wild type Rb protein. E2F is also co-precipitated with the cyclin A protein, reflecting the interaction of E2F with cyclin A during S phase of the cell cycle. Examples of such assays are shown in FIG. 8B using a U937 cell extract as the source of the E2F-Rb and the E2F-cyclin A complexes. E2F is clearly detected in immunoprecipitates employing either the Rb antibody or the cyclin A antibody. In sharp contrast to the result with the U937 extract, there was no evidence of the co-immunoprecipitation of E2F with Rb from extracts of C-33A and HT3 cells, both of which lack a functional Rb protein (FIG. 8B). E2F was, however, readily detected in cyclin A immunoprecipitates using these same extracts. Assays for the E2F-Rb complex in the cervical carcinoma cells that possess a normal Rb but express HPV E7 demonstrated a general lack of the E2F-Rb complex. The one exception was the SiHa cell extract in which E2F was recovered in the Rb-specific immunoprecipitate, although the amount was reduced in comparison to that obtained from the U937 extract. Once again, immunoprecipitation of these same extracts with a cyclin A antiserum demonstrated that the E2F-cyclin A interaction persisted in most of the cells, although in some cases the level was reduced (for instance, the HeLa cell sample). Therefore, assays for E2F in the cervical carcinoma extracts, either by direct gel retardation or by co-immunoprecipitation, demonstrate a general loss of the interaction with the Rb protein, a variable reduction in the interaction with cyclin A, and a uniform increase in the level of free E2F.

The results presented here demonstrate that the HPV E7 protein can also disrupt the E2F-Rb complex, dependent on the domain homologous to conserved region 2 of adenovirus E1A. Perhaps of most significance is the observation that the E2F-Rb complex is absent from most of the cervical carcinoma cell lines that express E7, thus providing in vivo evidence for the action of E7 to disrupt E2F-Rb. Moreover, the analysis of the human cervical carcinoma cell lines described here supports the hypothesis that the disruption of the E2F-Rb complex, either through the action of the HPV E7 protein or through mutation of the Rb protein, is an important event in the genesis of human cervical cancer.

The foregoing examples are illustrative of the present invention, and are not to be construed as limiting thereof. The invention is defined by the following claims, with equivalents of the claims to be included therein.

That which is claimed is:

1. A diagnostic assay for detecting the disruption of E2F-Rb complex formation and thereby determining the oncogenic state of cells, in a human or animal subject, comprising:

collecting a cell sample from said subject; and then detecting E2F free of the Retinoblastoma (Rb) protein or the E2F-Rb complex in said cell sample, the presence of E2F free of the Rb protein coincident with the loss of the E2F-Rb complex indicating the loss of Rb function and the oncogenic state of said cells, while the presence of the E2F-Rb complex indicates normal Rb function and a normal oncogenic state of said cells.

2. A method according to claim 1, wherein said cells are selected from the group consisting of cervical, retina, bone, lung, bladder, prostate, mammary, and white blood cells.

3. A method according to claim 1, wherein said cells are cervical cells.

4. A method according to claim 1, wherein said cells are retina cells.

5. A method according to claim 1, wherein said cells are bone cells.

6. A method according to claim 1, wherein said cells are lung cells.

7. A method according to claim 1, wherein said cells are prostate cells.

8. A method according to claim 1, wherein said cells are mammary tissue cells.

9. A method according to claim 1, wherein said cells are white blood cells.

10. A method according to claim 1, wherein said cells are human cells.

11. A method according to claim 1, wherein said detecting step is carried out by an assay procedure selected from the group consisting of immunoassay, affinity binding assay, and gel retardation assay.

12. A method according to claim 1, wherein said subject has not previously been diagnosed as carrying cancer.

13. A method according to claim 1, wherein said cell sample is collected from a tissue suspected of harboring a cancer.

14. An in vitro assay for screening test compounds for the ability to prevent the disruption of the Rb-E2F complex and to inhibit or reverse the oncogenic state of cells, comprising:

adding a test compound to an aqueous solution containing a complex of the Retinoblastoma (Rb) protein and a DNA tumor virus oncoprotein which binds to the Rb protein, said DNA tumor virus oncoprotein being capable of disrupting complex formation between said Rb protein and the E2F transcription factor; then adding the E2F transcription factor to the aqueous solution; and then detecting the formation of a complex of the Rb protein and the E2F transcription factor;

the formation of said complex indicating the ability of the compound to prevent the disruption of the Rb-E2F complex and to inhibit the oncogenic state of said cells.

15. A method according to claim 14, wherein said DNA tumor virus oncoprotein is selected from the group consisting of adenovirus and human papillomavirus viral oncoproteins.

16. A method according to claim 14, wherein said DNA tumor virus oncoprotein is the E7 viral oncoprotein.

17. A method according to claim 14, wherein said detecting step is carried out by an assay procedure selected from the group consisting of immunoassay, affinity binding assay, and gel retardation assay.

18. A bioassay for screening test compounds for the ability to prevent the disruption of the Rb-E2F complex and to inhibit or reverse the oncogenic state of cells, comprising:

contacting a test compound with a cell capable of producing a complex of the Retinoblastoma (Rb) protein and the E2F transcription factor, and wherein said cell contains a DNA tumor virus expressing a viral oncoprotein which binds to the Rb protein and is capable of disrupting said complex; and then detecting the loss of E2F free of the Rb protein in said cells, and the appearance of the E2F-Rb complex, the appearance of increased levels of the E2F-Rb complex indicating the compound's ability to prevent the disruption of the Rb-E2F complex and to inhibit or reverse the oncogenic state of said cells.

19. A method according to claim 18, wherein said cells are human cells.

20. A method according to claim 18, wherein said DNA tumor virus is selected from the group consisting of adenovirus and human papillomavirus.

21. A method according to claim 18, wherein said cells are human cervical cells and said virus is human papillomavirus.

22. A method according to claim 18, wherein said contacting step is carried out in vitro in an aqueous solution.

23. A method according to claim 18, wherein said detecting step is carried out by an assay procedure selected from the group consisting of immunoassay, affinity binding assay, and gel retardation assay.

\* \* \* \* \*

UNITED STATES PATENT AND TRADEMARK OFFICE
CERTIFICATE OF CORRECTION

PATENT NO. : 5,650,287
DATED : July 22, 1997
INVENTOR(S) : Joseph R. Nevins and Srikumar P. Chellappan It is certified that error appears in the above-identified patent and that said Letters Patent is hereby corrected as shown below:

Title page, item [73], "Assignee" please insert --Duke University--.

Title page, under "Attorney, Agent, or Firm" please insert --Bell, Seltzer, Park & Gibson--.

Signed and Sealed this

Seventh Day of July, 1998

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,650,287
DATED : July 22, 1997
INVENTOR(S) : Joseph R. Nevins and Srikumar P. Chellappan It is certified that error appears in the above-identified patent and that said Letters Patent is hereby corrected as shown below:

On the title page, inem [73] should read:

"Assignee " --Duke University, Durham NC--.

Signed and Sealed this

Twenty-third Day of March, 1999

Attest:

Q. TODD DICKINSON

*Attesting Officer*     *Acting Commissioner of Patents and Trademarks*